US010489939B2

(12) United States Patent
Xing et al.

(10) Patent No.: US 10,489,939 B2
(45) Date of Patent: Nov. 26, 2019

(54) SPECTRAL CT IMAGE RECONSTRUCTING METHOD AND SPECTRAL CT IMAGING SYSTEM

(71) Applicants: TSINGHUA UNIVERSITY, Beijing (CN); Nuctech Company Limited, Beijing (CN)

(72) Inventors: Yuxiang Xing, Beijing (CN); Li Zhang, Beijing (CN); Huayu Zhang, Beijing (CN); Le Shen, Beijing (CN)

(73) Assignees: TSINGHUA UNIVERSITY, Beijing (CN); NUCTECH COMPANY LIMITED, Beijing (CN)

( * ) Notice: Subject to any disclaimer, the term of this patent is extended or adjusted under 35 U.S.C. 154(b) by 0 days.

(21) Appl. No.: 15/580,005

(22) PCT Filed: Aug. 22, 2016

(86) PCT No.: PCT/CN2016/096191
§ 371 (c)(1),
(2) Date: Dec. 6, 2017

(87) PCT Pub. No.: WO2017/041620
PCT Pub. Date: Mar. 16, 2017

(65) Prior Publication Data
US 2018/0182129 A1    Jun. 28, 2018

(30) Foreign Application Priority Data
Sep. 9, 2015 (CN) .......................... 2015 1 0572013

(51) Int. Cl.
*G06T 11/00* (2006.01)
*G06T 7/00* (2017.01)
(52) U.S. Cl.
CPC .......... *G06T 11/005* (2013.01); *G06T 7/0012* (2013.01); *G06T 2207/10081* (2013.01);
(Continued)

(58) Field of Classification Search
CPC combination set(s) only.
See application file for complete search history.

(56) References Cited

U.S. PATENT DOCUMENTS

| 6,907,102 B1* | 6/2005 | Sauer | A61B 6/032 |
| | | | 378/19 |
| 2006/0285632 A1* | 12/2006 | Boese | A61B 6/032 |
| | | | 378/8 |

(Continued)

FOREIGN PATENT DOCUMENTS

| CN | 1300938 A | 6/2001 |
| CN | 1865954 A | 11/2006 |

(Continued)

OTHER PUBLICATIONS

International Search Report dated Nov. 30, 2016 issued in PCT/CN2016/096191.

(Continued)

*Primary Examiner* — Tsung Yin Tsai
(74) *Attorney, Agent, or Firm* — Scully Scott Murphy & Presser, P.C.

(57) ABSTRACT

A spectral CT image reconstructing method includes: collecting incomplete original projection data in each of a plurality of energy windows; performing a projection data cross estimation using corresponding original projection data in at least one pair of energy windows constituted by different energy windows of the plurality of energy windows to obtain estimated projection data, wherein each pair of energy windows comprises a first energy window and a second energy window; combining the original projection data and the corresponding estimated projection data to obtain complete projection data; and reconstructing a spectral CT image using the complete projection data.

8 Claims, 10 Drawing Sheets

(52) U.S. Cl.
    CPC ............... *G06T 2207/20081* (2013.01); *G06T 2211/408* (2013.01)

(56) References Cited

U.S. PATENT DOCUMENTS

| | | | |
|---|---|---|---|
| 2007/0242796 A1* | 10/2007 | Vengrinovich | G06T 11/006 378/11 |
| 2008/0013676 A1 | 1/2008 | Bontus et al. | |
| 2008/0205737 A1* | 8/2008 | Kunze | G06T 11/006 382/131 |
| 2009/0092219 A1* | 4/2009 | Wu | A61B 6/032 378/5 |
| 2010/0189212 A1* | 7/2010 | Zou | G06T 11/005 378/5 |
| 2010/0215233 A1* | 8/2010 | Hsieh | A61B 6/032 382/131 |
| 2010/0284596 A1* | 11/2010 | Miao | G06T 11/005 382/131 |
| 2014/0369458 A1 | 12/2014 | Shen et al. | |
| 2016/0202364 A1* | 7/2016 | Wang | A61B 6/032 378/5 |

FOREIGN PATENT DOCUMENTS

| | | |
|---|---|---|
| CN | 102362292 A | 2/2012 |
| CN | 102947864 A | 2/2013 |
| CN | 103339657 A | 10/2013 |
| CN | 103913472 A | 7/2014 |
| CN | 104240270 A | 12/2014 |
| CN | 104323789 A | 2/2015 |
| WO | 2012/104740 A1 | 8/2012 |
| WO | 2016/093917 A1 | 6/2016 |

OTHER PUBLICATIONS

Yu L. et al., "Pre-Reconstruction Three-Material Decomposition in Dual-Energy CT", Proceedings of SPIE 7258:72583V-72583V-8 (Feb. 26, 2009).

Zhang H. et al., "Reconstruction of Limited-Angle Dual-Energy CT Using Mutual Learning and Cross-Estimation (MLCE)", Proceedings of SPIE 9873:978344-978344 (Mar. 30, 2016).

Extended Supplementary European Search Report dated Mar. 1, 2019 received in European Application No. 16 84 3558.4.

* cited by examiner

SPECTRAL CT IMAGE RECONSTRUCTING METHOD AND SPECTRAL CT IMAGING SYSTEM

CROSS REFERENCE

This application is the 371 application of PCT Application No. PCT/CN2016/096191 filed Aug. 22, 2016, which is based on and claims priority to Chinese Patent Application No. 201510572013.0, filed Sep. 9, 2015, the entire contents of which are incorporated herein by reference.

TECHNICAL FIELD

The present disclosure relates to the field of spectral CT imaging technologies, and more particularly, to a spectral CT image reconstructing method and a spectral CT imaging system based on machine learning and projection domain estimation.

BACKGROUND

Dual-energy CT was put forward in the 1970s. With the development of X-ray detectors and imaging systems, dual-energy CT is widely used. In recent years, with the development of technologies related to detectors and further demands for CT imaging, spectral CT using dual-energy or multi-energy (i.e., X-ray with two and more energy spectrums is employed to pass through objects to form signals for imaging, which is generally referred to as X-ray of a plurality of energy windows or energy channels) attracts widespread attention and flourishes in practical application. Compared with traditional mono-energy CT, the spectral CT not only gets rid of defects of spectrum hardening and insufficient contrast, but also can distinguish materials, especially materials with the same absorption coefficient at certain energies. These advantages make the spectral CT available for numerous clinical applications such as abdominal imaging and lung disease detection, etc.

In general, the spectral CT at each energy needs to collect complete CT data. Taking the fan-beam CT as an example, a complete projection dataset should cover a short-scan angle (180 degrees plus a fan-beam angle). The traditional multi-energy data collection requires a short scan at different energies for many times; or a dual-source or multi-source CT are employed to perform a single scan; or an energy resolution detector such as a photon-counting detector is employed to perform a single scan to acquire multi-energy projection data. The above solutions may encounter problems such as increased radiation dose, long scanning time and high hardware cost, etc.

One solution is to avoid collecting complete CT data. However, this solution is faced with a problem of inadequate projection data for reconstruction. For this reason, according to a general solution, compression sensing technologies are employed. That is, supposing the signal is sparse or becomes sparse in a transform domain, namely $$\|\Psi(x)\|_0 \leq s \quad (1)$$

wherein $x \in R^n$ denotes an original signal, $\Psi(\cdot)$ denotes a sparse operator, and s denotes sparseness. In practical application, generally L0 norm is replaced with L1 norm, which changes the problem into a convex programming problem, wherein A denotes a forward projection, and b denotes measured projection data:

$$\operatorname{argmin}_x \|\Psi(x)\|_1 \text{ s.t. } Ax=b \quad (2)$$

However, an improved spectral CT image reconstruction algorithm is still required.

The above-mentioned information disclosed in this Background section is only for the purpose of enhancing the understanding of background of the present disclosure and may therefore include information that does not constitute a prior art that is known to those of ordinary skill in the art.

SUMMARY

This application discloses a spectral CT image reconstructing method based on machine learning and projection domain estimation, which can solve the foregoing reconstruction problem.

Other features and advantages of the present disclosure will become apparent from the following detailed description, or in part, by practice of the present disclosure.

According to an aspect of the present disclosure, there is provided a spectral CT image reconstructing method, including: collecting incomplete original projection data in each of a plurality of energy windows; performing a projection data cross estimation using corresponding original projection data in at least one pair of energy windows constituted by different energy windows of the plurality of energy windows to obtain estimated projection data, wherein each pair of energy windows includes a first energy window and a second energy window; combining the original projection data with the corresponding estimated projection data to obtain complete projection data; and reconstructing a spectral CT image using the complete projection data.

According to another aspect of the present disclosure, there is provided a spectral CT imaging system, including: a ray generating device, including a ray source; a photon-counting detector or an energy-sensitive detector, including a plurality of pixels; a data collecting system, configured to perform data collection on a photon passing through an imaged object from the photon-counting detector or energy-sensitive detector; and an image reconstruction system, configured to reconstruct a spectral CT image using data acquired by the data collecting system. The data collecting system is configured to collect incomplete original projection data in each of a plurality of energy windows. The image reconstruction system includes: a cross estimation module, configured to perform a projection data cross estimation using corresponding original projection data in at least one pair of energy windows constituted by different energy windows of the plurality of energy windows to obtain estimated projection data, wherein each pair of energy windows includes a first energy window and a second energy window; a combining module, configured to combine the original projection data with the corresponding estimated projection data to obtain complete projection data; and a reconstructing module, configured to reconstruct the spectral CT image using the complete projection data.

According to another aspect of the present disclosure, there is provided a non-transitory computer-readable storage medium having stored therein instructions that, when executed by a processor of a spectral CT imaging system, causes the system to perform a spectral CT image reconstructing method, the method including: collecting incomplete original projection data in each of a plurality of energy windows; performing a projection data cross estimation using corresponding original projection data in at least one pair of energy windows constituted by different energy windows of the plurality of energy windows to obtain estimated projection data, wherein each pair of energy windows comprises a first energy window and a second energy window; combining the original projection data with the corresponding estimated projection data to obtain complete projection data; and reconstructing a spectral CT image using the complete projection data.

Using the spectral CT image reconstructing method according to some embodiments of the present disclosure, a relation between spectral CT absorption coefficients is learned using, for example, an artificial neural network, and then projection data not collected are estimated. In this way, the problem of inadequate projection data for reconstruction can be solved.

This section provides a summary of various implementations or examples of the technology described in the disclosure, and is not a comprehensive disclosure of the full scope or all features of the disclosed technology.

BRIEF DESCRIPTION OF THE DRAWINGS

The above and other features and advantages of the present disclosure will become more apparent by describing in detail the exemplary embodiments thereof with reference to the accompanying drawings.

DETAILED DESCRIPTION

The exemplary embodiment will now be described more fully with reference to the accompanying drawings. However, the exemplary embodiments can be implemented in a variety of forms and should not be construed as limited to the embodiments set forth herein. Rather, the embodiments are provided so that this disclosure will be thorough and complete and will fully convey the concepts of exemplary embodiments to those skilled in the art. The same reference numerals in the drawings denote the same or similar parts, and thus repeated description thereof will be omitted.

In addition, the features, structures, or characteristics described may be combined in one or more embodiments in any suitable manner. In the following description, numerous specific details are provided to give a full understanding of the embodiments of the present disclosure. However, those skilled in the art will appreciate that one or more of the specific details may be practiced without practicing the technical solutions of the present disclosure, and other methods, components, materials, devices, steps, and the like may be employed. In other instances, well-known structures, methods, devices, implementations, materials, or operations are not shown or described in detail to avoid obscuring aspects of the present disclosure.

The block diagrams illustrated in the drawings are merely functional entities and do not necessarily correspond to any physically separate entity. In other words, these functional entities may be implemented in software form, or implemented in one or more hardware modules or integrated circuits, or implemented in different networks and/or processor devices and/or microcontroller devices.

The flowcharts as shown in the accompanying drawings are merely exemplary description instead of necessarily including all the steps. For example, some steps may be broken down, while some steps may be combined or partly combined. Therefore, the actual execution sequences may be changed according to the actual conditions.

According to the inventive concepts of the prevent disclosure, projection data cross estimation is performed using pairwise data in different energy windows.

Figure 1:
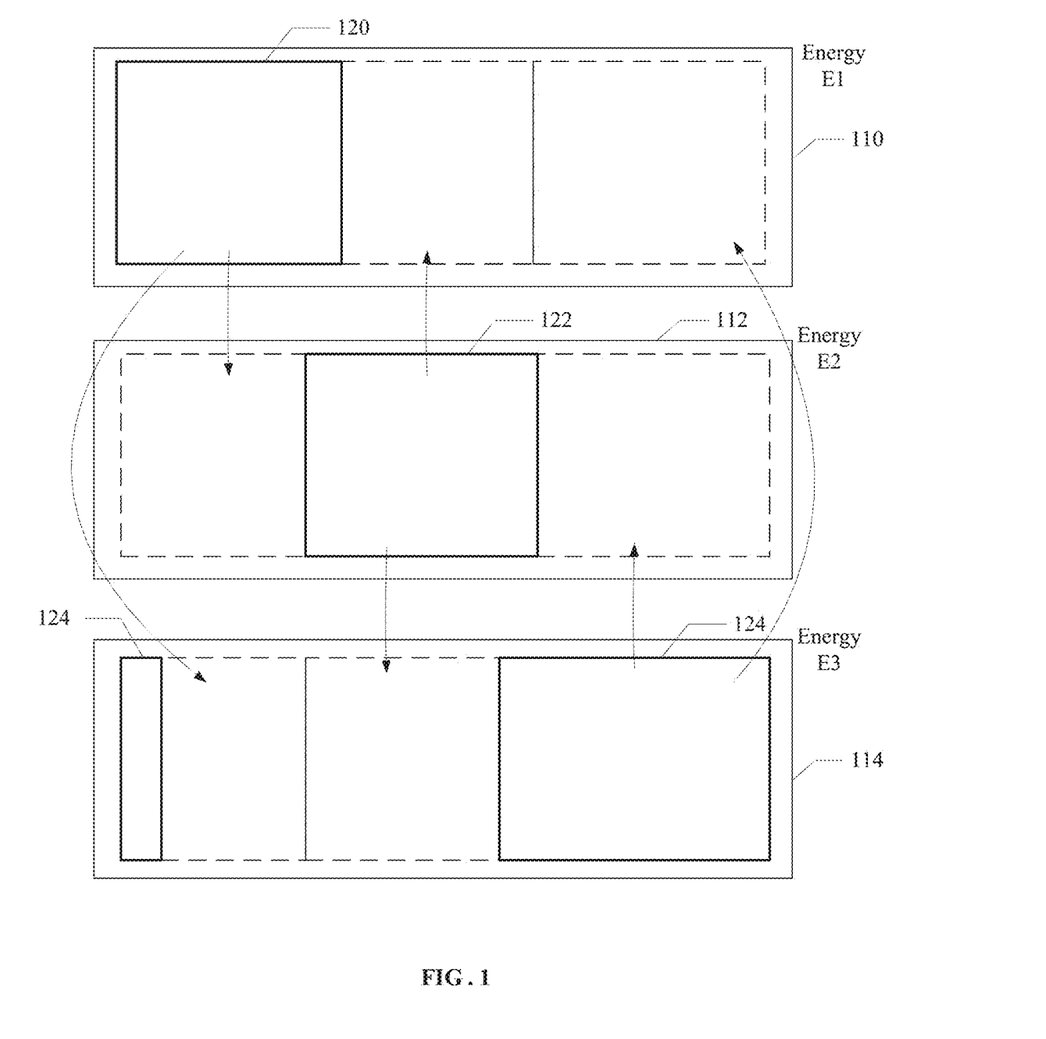
FIG. 1 illustrates cross estimation of data space in paired energy windows in an exemplary system of three energy windows.

FIG. 1 illustrates cross estimation of data space in paired energy windows in an exemplary system of three energy windows.

Referring to the system of the three energy windows as shown in FIG. 1, the outermost solid line boxes 110, 112 and 124 represent complete data space corresponding to CT projection data in each energy, the solid line boxes 120, 122 and 124 represent data space corresponding to incomplete data actually collected in each energy, the dashed line boxes represent data space occupied by estimated data obtained from cross estimation. The arrows indicate directions of the cross estimation.

Only a part of data are collected in each energy window: energies $E_1$ and $E_2$ are used as a pair, and cross estimation is performed on a part of missing data in energy $E_1$ and a part of missing data in energy $E_2$; energies $E_1$ and $E_3$ are used as a pair, and cross estimation is performed on a part of missing data in energy E and a part of missing data in energy $E_3$; and also energies $E_2$ and $E_3$ may be used as a pair, and cross estimation is performed on a part of missing data in energy $E_2$ and a part of missing data in energy $E_3$.

A method of projection data cross estimation is illustrated below by taking any pair of energies $E_k$ and $E_{k'}$ as an example.

In this method, projection data collected at $E_k$ and $E_{k'}$ whose projections pass through an identical ray path are extracted to determine a mapping relation. Herein, a projection consistent with a ray direction may be used, or projections of conjugate rays may be used.

Supposing equivalent linear attenuation coefficient images at a pair of energies are $f_{E_k} = \{f_{E_k,1}, f_{E_k,2}, L, f_{E_k,N}\}$ and $f_{E_{k'}} = \{f_{E_{k'},1}, f_{E_{k'},2}, L, f_{E_{k'},N}\}$, projection data obtained through CT scanning at each energy respectively are $p_{E_k} = \{p_{E_k,1}, p_{E_k,2}, L, p_{E_k,M_k}\}$, with corresponding data space being denoted by $\Omega_k$, and $p_{E_{k'}} = \{p_{E_{k'},1}, p_{E_{k'},2}, L, p_{E_{k'},M_k}\}$, with corresponding data space being denoted by $\Omega_{k'}$. Line integral projection operators are denoted by $$H_{E_k} = \{h_{E_k,ij}\}_{M_k \times N} \text{ and } H_{E_{k'}} = \{h_{E_{k'},ij}\}_{M_{k'} \times N}.$$

The problem for directly performing iterative reconstruction is as follows:

$$\min \|H_E f_E - p_E\|_2^2 = \min(H_E f_E - p_E)^T(H_E f_E - p_E) \quad (3)$$

wherein E corresponds to $E \in \{E_k, E_{k'}\}$, N represents the number of pixels of a reconstructed image, $M_k$ and $M_{k'}$ represent the number rays, if represent elements of a matrix corresponding to an i-th ray and a j-th pixel respectively. The equation is ill-conditioned because $M_k$, $M_{k'} < N$ in the projection matrix. In the present disclosure, by establishing a mapping from the projection data at $E_k$ to the projection data at $E_{k'}$, or a mapping from the projection data at $E_{k'}$ to the projection data at $E_k$, $$\varphi_{E_k,E_{k'}} : p_{E_k} \to p_{E_{k'}}$$

$$\varphi_{E_{k'},E_k} : p_{E_{k'}} \to p_{E_k} \quad (4)$$

the projection $p_{E_{k'}}^{crs}$ of $E_{k'}$ in space $\Omega_k$ and the projection $p_{E_k}^{crs}$ of $E_k$ in space $\Omega_{k'}$ may be estimated, so that projection information may be increased, and ill-condition of the equation may be weakened. Because the mapping relation on a projection domain is not apparent, in the present disclosure, an indirect mapping relation established on the image domain is $\psi_{E_k,E_{k'}} : f_{E_k} \to f_{E_{k'}} (\psi_{E_{k'},E_k} : f_{E_{k'}} \to f_{E_k})$, so that the projection domain mapping may be expressed as:

$$p_{E_{k'}} = \varphi_{E_k,E_{k'}}(p_{E_k}) = R(\psi_{E_k,E_{k'}}(R^{-1}(p_{E_k}))) \quad (5)$$

wherein the R is projection transformation on a continuous domain, which corresponds to the projection matrix H of a discrete domain. $\psi_{E_k,E_{k'}}$ and $\psi_{E_{k'},E_k}$ may be obtained using a machine learning method, for example, using an artificial neural network method. The projection data passing through an identical ray path collected from the projection at $E_k$ and $E_{k'}$ may be used as training data to obtain mapping relations $\psi_{E_k,E_{k'}}$ and $\psi_{E_{k'},E_k}$.

Figure 2:
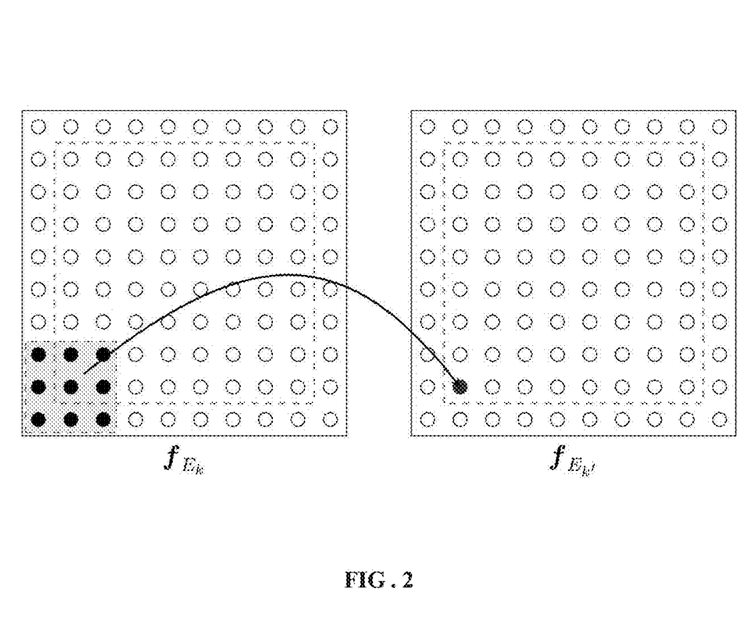
FIG. 2 illustrates a schematic diagram of image mapping.
Figure 3:
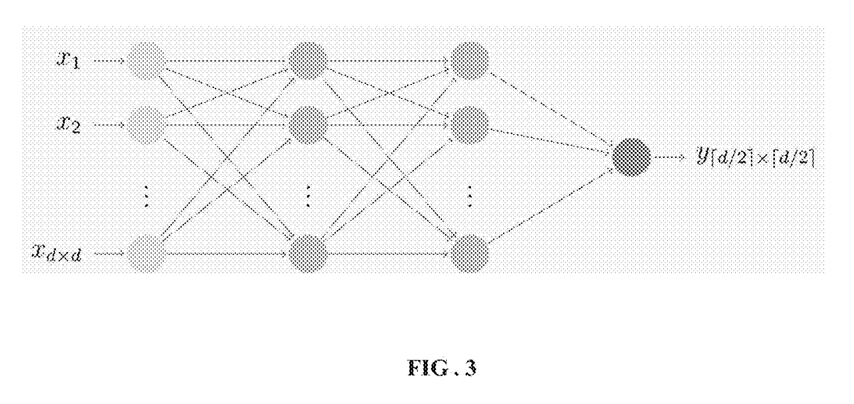
FIG. 3 illustrates a schematic diagram of learning taking a two-layer artificial neural network, where each layer has ten nodes (neurons), as an example.

For example, at first, images $f_{E_k}^{cgs}$ and $f_{E_{k'}}^{cgs}$ are reconstructed using the projection data $p_{E_k}^{crs}$ and $p_{E_{k'}}^{crs}$ passing through the identical ray path, and then pixel-by-pixel learning is performed on the images, $$f_{E_{k'}}(n) = \psi_{E_k,E_{k'}}(f_{E_k}(N)), N = \text{Neighbor}(n) \quad (6)$$

wherein n is a pixel subscript n=1, 2, ..., N, and N is a d×d neighbor domain taking the n as a center. f(N) is taken as an input of the artificial neural network, and f(n) is taken as an output. FIG. 2 illustrates a schematic diagram of image mapping. FIG. 3 illustrates a schematic diagram of learning taking a two-layer artificial neural network, where each layer has ten nodes (neurons), as an example. Mapping relations $\psi_{E_k,E_{k'}}$ and $\psi_{E_{k'},E_k}$ are known, it is estimated:

$$p_{E_{k'}}^{crs} = R(\psi_{E_k,E_{k'}}(R^{-1}(p_{E_k})))$$

$$p_{E_k}^{crs} = R(\psi_{E_{k'},E_k}(R^{-1}(p_{E_{k'}}))) \quad (7)$$

Complete projection data may be obtained by combining the estimated projection data with the original projection data:

$$p_{E_k}^{whole} = \begin{pmatrix} p_{E_k} \\ p_{E_k}^{crs} \end{pmatrix} \quad p_{E_{k'}}^{whole} = \begin{pmatrix} p_{E_{k'}}^{crs} \\ p_{E_{k'}} \end{pmatrix} \quad (8)$$

The original data are almost doubled, and the projection data in Formula (8) are employed for the final reconstruction. In this way, a dual-energy CT image having a higher quality may be obtained.

Figure 4:
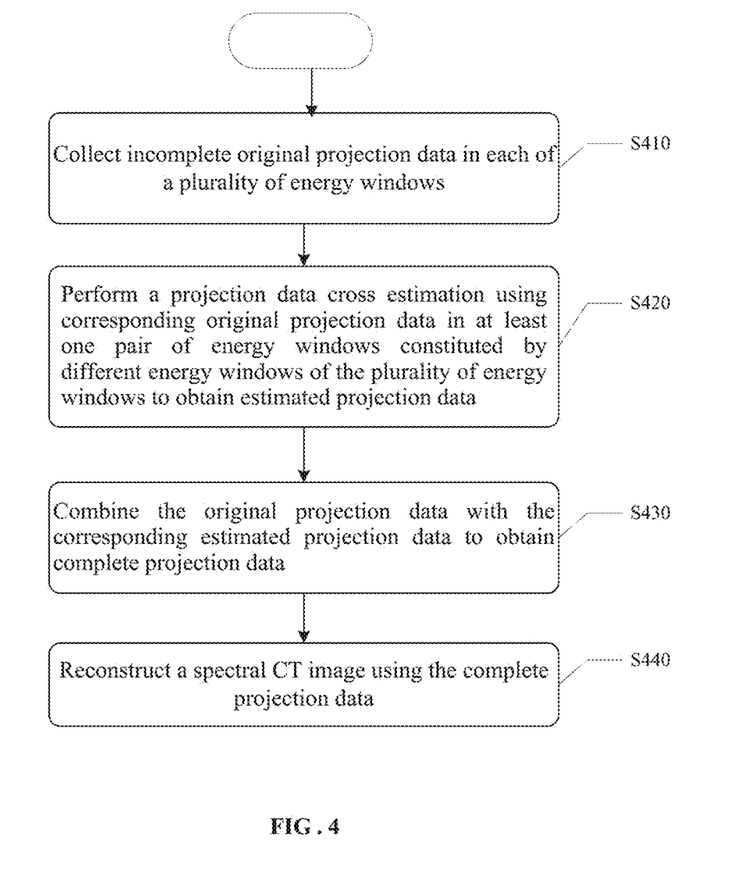
FIG. 4 illustrates a flowchart of a spectral CT image reconstructing method based on the above conception according to an embodiment of the present disclosure.

FIG. 4 illustrates a flowchart of a spectral CT image reconstructing method based on the above conception according to an embodiment of the present disclosure.

As shown in FIG. 4, in S410, incomplete original projection data in each of a plurality of energy windows are collected. For example, the incomplete original projection data may be collected by means of limited angle sampling, angle sparse sampling, or sparse detector sampling.

In S420, a projection data cross estimation is performed using corresponding original projection data in at least one pair of energy windows constituted by different energy windows of the plurality of energy windows to obtain estimated projection data. Each pair of energy windows includes a first energy window and a second energy window.

For example, a mapping relation between image data in the first energy window and image data in the second energy window may be established on an image domain.

The mapping relation may be established by means of a machine learning method. For example, first training image data are obtained by reconstructing using the first identical projection data, and second training image data are obtained by reconstructing using the second identical projection data. Next, a first mapping relation $\psi_{E_k,E_{k'}}$ from the image data in the first energy window to the image data in the second energy window and/or a second mapping relation $\psi_{E_{k'},E_k}$ from the image data in the second energy window to the image data in the first energy window are established by means of a machine learning method using the first training image data and the second training image data. The machine learning method may be, for example, an artificial neural network method, but the present disclosure is not limited thereto.

Next, estimated image data may be obtained using the mapping relation. For example, first initial image data and/or second initial image data are respectively obtained by reconstructing in advance using the corresponding original projection data in the first energy window and the second energy window. Next, second estimated image data in the second energy window are obtained by mapping the first initial image data by means of the first mapping relation, and first estimated image data in the first energy window are obtained by mapping the second initial image data by means of the second mapping relation.

Next, the estimated projection data are obtained from the estimated image data. For example, first estimated projection data are obtained using the first estimated image data and a projection operator used in the first energy window, and second estimated projection data are obtained using the second estimated image data and a projection operator used in the second energy window.

In S430, the original projection data are combined with the corresponding estimated projection data to obtain complete projection data.

In S440, a spectral CT image is reconstructed using the complete projection data.

Figure 5:
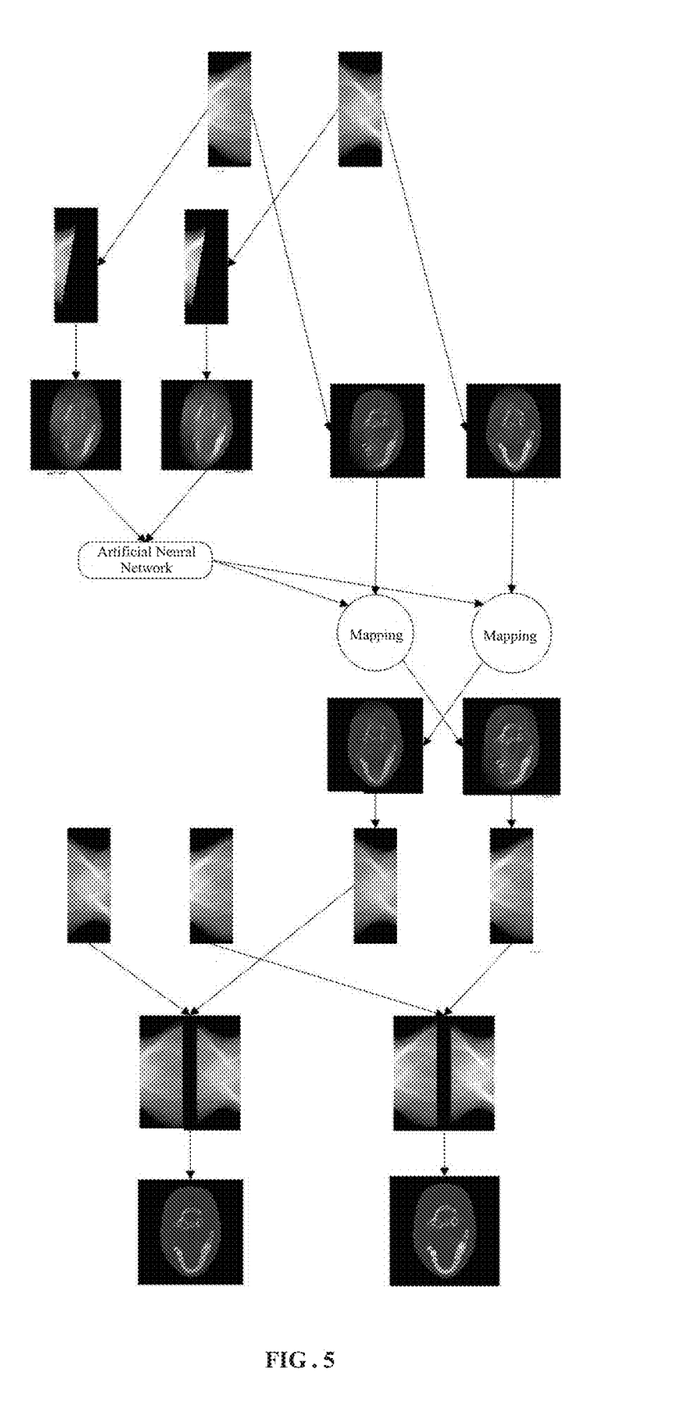
FIG. 5 illustrates an example procedure of performing cross estimation and image reconstruction according to an embodiment of the present disclosure.
Figure 6:
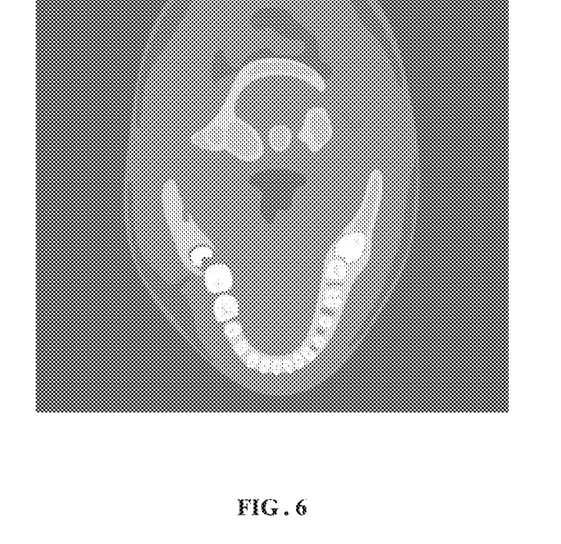
FIG. 6 is a dental model used in the example procedure of FIG. 5.
Figure 7:
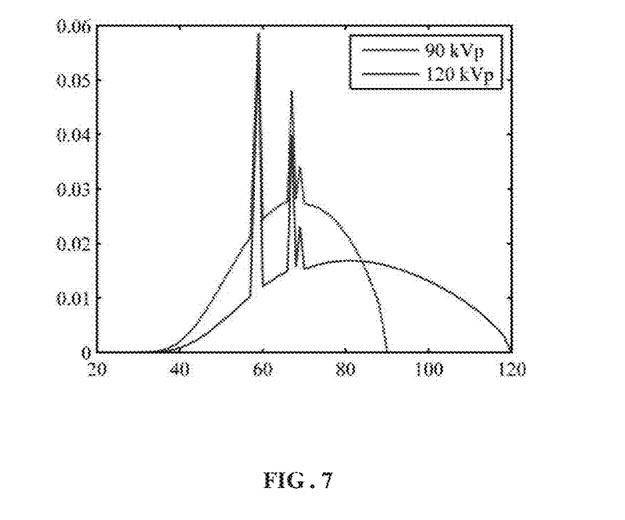
FIG. 7 is a CT spectrum used in the example procedure of FIG. 5.
Figure 8:
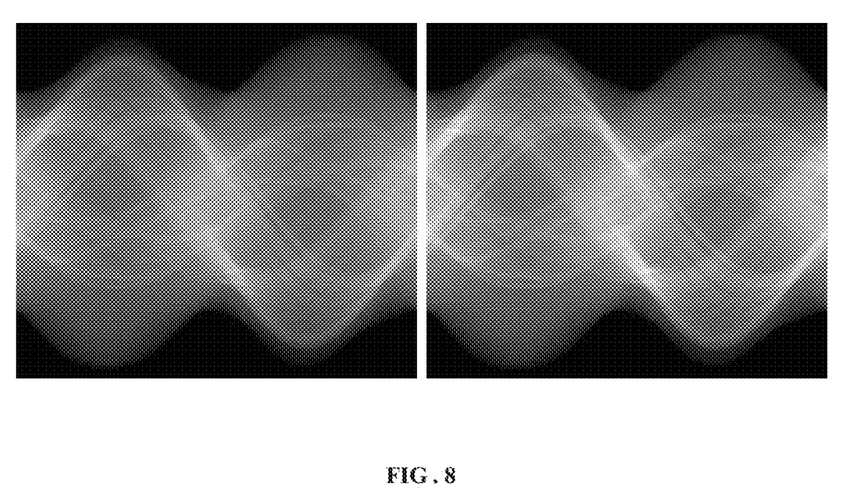
FIG. 8 is complete projection data of the dental model of FIG. 6.

FIG. 5 illustrates an example procedure of performing cross estimation and image reconstruction according to an embodiment of the present disclosure. FIG. 6 is a dental model used in the example procedure of FIG. 5. FIG. 7 is a CT spectrum used in the example procedure of FIG. 5. FIG. 8 is complete projection data of the dental model of FIG. 6.

(1) Projection data $p_{E_k}$ and $p_{E_{k'}}$ passing through an identical ray path are extracted from the original projection data $p_{E_k}^{cgs}$ and $p_{E_{k'}}^{cgs}$, and training image data $f_{E_k}^{cgs}$ and $f_{E_{k'}}^{cgs}$ are obtained using a universal reconstruction method such as filtered back-projection reconstruction or iterative reconstruction, which is not unnecessarily described herein.

(2) The training image data $f_{E_k}^{cgs}$ and $f_{E_{k'}}^{cgs}$ are respectively used as input and a target, and the artificial neural network learning is employed to obtain mapping $\psi_{E_k,E_{k'}}$: $f_{E_k} \to f_{E_{k'}}, \psi_{E_{k'},E_k}: f_{E_{k'}} \to f_{E_k}$.

(3) Reconstruction is performed in advance using the projection data $p_{E_k}$ and $p_{E_{k'}}$, and the initial image data $f_{E_k}^{init}$ and $f_{E_{k'}}^{init}$ are obtained according to, for example, Formula (3).

(4) Cross estimation, estimated image data are obtained using the mapping relation:

$$f_{E_{k'}}^{crs} = \psi_{E_k,E_k}(f_{E_k}^{init})$$

$$f_{E_k}^{crs} = \psi_{E_k,E_k}(f_{E_{k'}}^{init}) \quad (9)$$

(5) Projection, the estimated projection data are obtained from the estimated image data:

$$p_{E_k}^{crs} = H_{E_k} f_{E_k}^{crs}$$

$$p_{E_{k'}}^{crs} = H_{E_{k'}} f_{E_{k'}}^{crs} \quad (10)$$

(6) The original projection data are combined with the estimated projection data:

$$p_{E_k}^{whole} = \begin{pmatrix} p_{E_k} \\ p_{E_k}^{crs} \end{pmatrix} \quad p_{E_{k'}}^{whole} = \begin{pmatrix} p_{E_{k'}}^{crs} \\ p_{E_{k'}} \end{pmatrix} \quad (11)$$

(7) Final reconstruction, complete data $p_{E_k}^{whole}$ and $p_{E_{k'}}^{whole}$ are employed for reconstruction, which is well-known to those skilled in the art, and thus is not described any more.

According to the embodiment, the model as shown in FIG. 6 and the dual-energy CT spectrum in FIG. 7 are employed, and the two dual-energy energies herein correspond to the pair of $E_k$ and $E_{k'}$ in the foregoing method to perform data cross estimation so as to respectively perform limited angle sampling, angle sparse sampling or sparse detector sampling.

Figure 9:
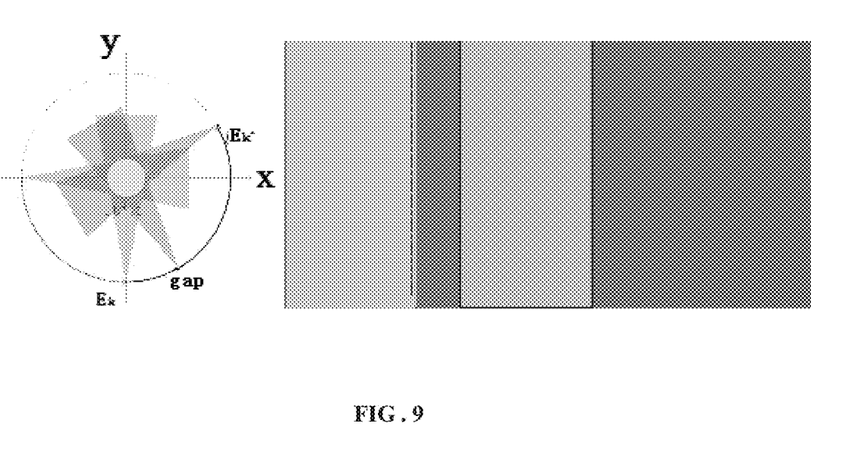
FIG. 9 illustrates a schematic diagram of limited angle sampling dual-energy CT scanning according to an embodiment of the present disclosure, wherein a left side is a scanning trace, and a right side is a schematic diagram of projection down-sampling.
Figure 12:
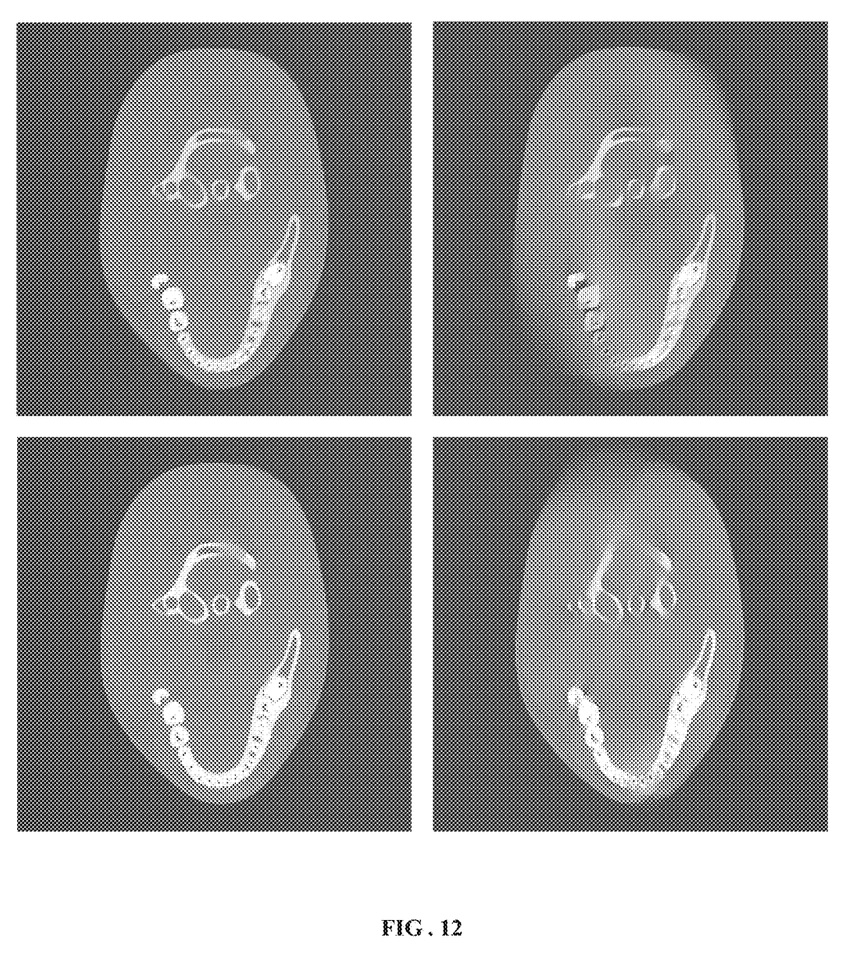
FIG. 12 illustrates a simulation result of performing image reconstruction on sampled data of FIG. 9 using the method of the present disclosure.

FIG. 9 illustrates a schematic diagram of limited angle sampling dual-energy CT scanning, wherein a left side is a scanning trace, and a right side is a schematic diagram of projection down-sampling. 512 detectors are employed for limited angle CT scanning, one sampling every other degree from 1 degree to 90 degrees at high energy, and one sampling every other degree from 120 degrees to 210 degrees at low energy. The reconstruction results are as shown in FIG. 12, wherein the left figure shows the result obtained according to the method of the present disclosure, and the right figure shows the result obtained by TV minimization constraint.

Figure 10:
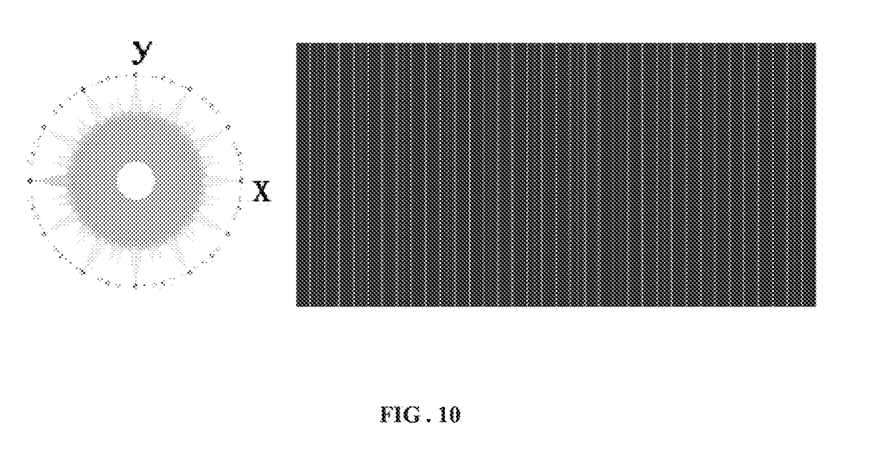
FIG. 10 illustrates a schematic diagram of angle sparse sampling CT scanning according to an embodiment of the present disclosure, wherein a left side is a scanning trace, and a right side is a schematic diagram of projection down-sampling.
Figure 13:
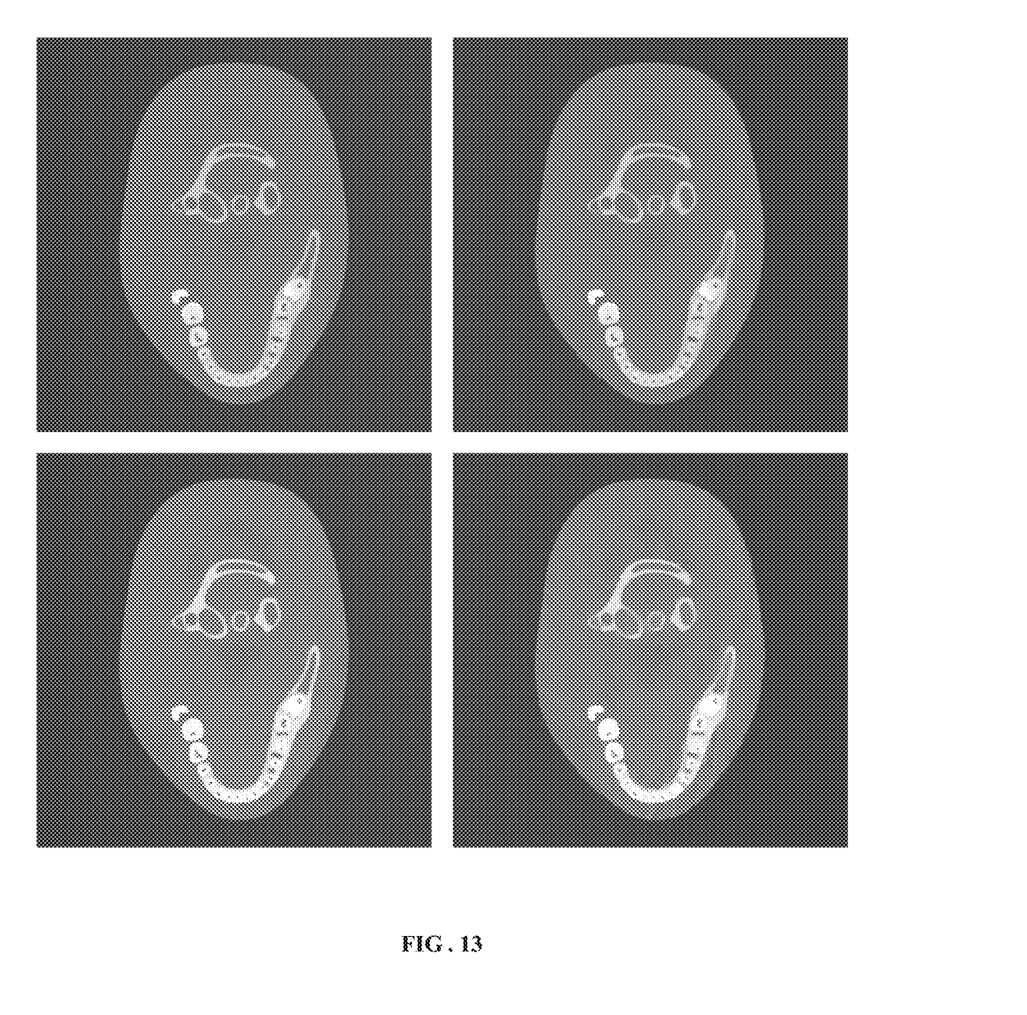
FIG. 13 illustrates a simulation result of performing image reconstruction on sampled data of FIG. 10 using the method of the present disclosure.

FIG. 10 illustrates a schematic diagram of angle sparse sampling CT scanning, wherein a left side is a scanning trace, and a right side is a schematic diagram of projection down-sampling. 512 detectors are employed for angle sparse sampling CT scanning, 36 angles $V_{E_k} = \{10°, 20°, \ldots, 360°\}$ are collected in a circle at high energy, and 24 angles $V_{E_{k'}} = \{15°, 30°, \ldots, 360°\}$ are collected in a circle at low energy. The reconstruction results are as shown in FIG. 13, wherein the left figure shows the result obtained according to the method of the present disclosure, and the right figure shows the result obtained by TV minimization constraint.

Figure 11:
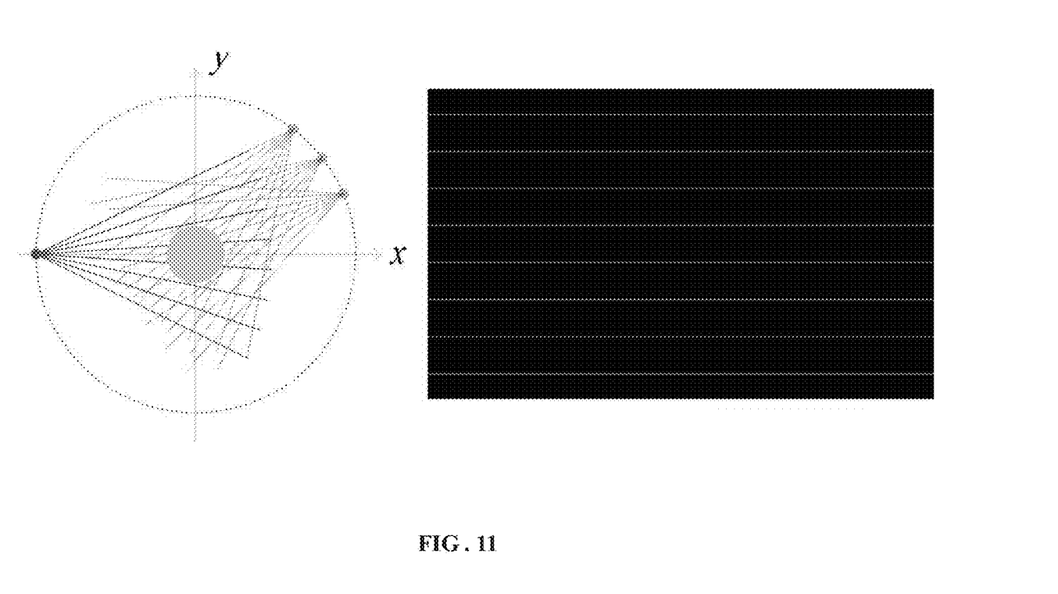
FIG. 11 illustrates a schematic diagram of detector sparse sampling CT scanning according to an embodiment of the present disclosure, wherein a left side is a scanning trace, and a right side is a schematic diagram of projection down-sampling.

FIG. 11 illustrates a schematic diagram of detector sparse sampling CT scanning, wherein a left side is a scanning trace, and a right side is a schematic diagram of projection down-sampling. There are 64 high energy detectors and 64 low energy detectors in a staggered arrangement. 360 projection angles are collected in a circle.

As can be seen from the above results, a data size required for reconstruction may be significantly reduced using the method according to the embodiment of the present disclosure, which is applicable to angle sparse sampling, sparse detector sampling and the like, so that the number of the detectors and a radiation dose may be decreased to reduce the manufacturing cost of a CT system. Furthermore, the method of the present disclosure also may be used for reducing an angle coverage to reduce a z axis layer thickness and improve the time resolution. In addition, the method according to the embodiment of the present disclosure may effectively inhibit artifacts possibly caused by reduction of data.

Figure 14:
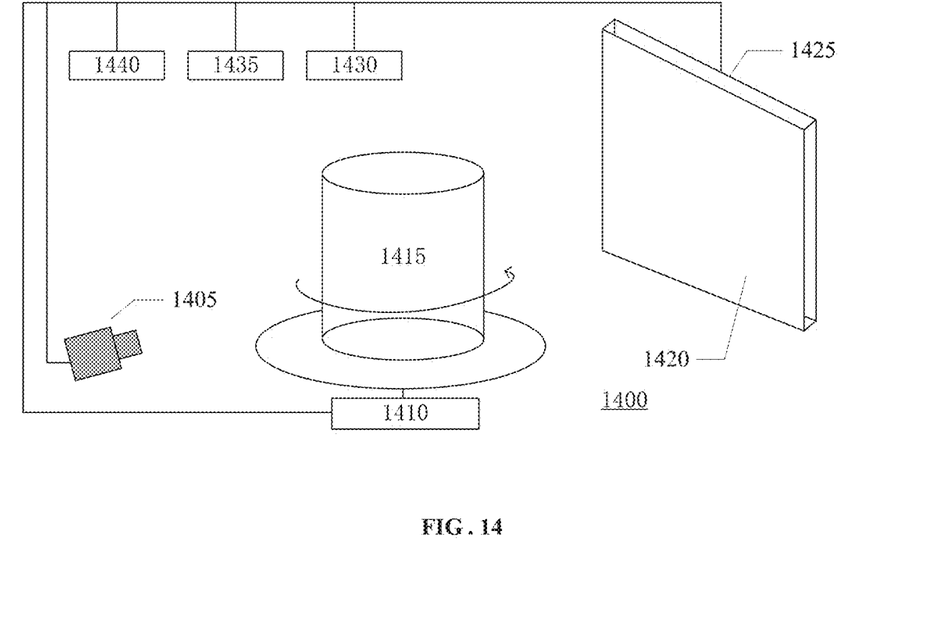
FIG. 14 schematically illustrates a schematic diagram of a system structure of a spectral CT imaging system according to some exemplary embodiments of the present disclosure.

FIG. 14 schematically illustrates a schematic diagram of a system structure of a spectral CT imaging system 1400 according to some exemplary embodiments of the present disclosure.

As shown in FIG. 14, the spectral CT imaging system 1400 may include a ray generating device 1405, a mechanical movement system 1410, a photon-counting detector or energy-sensitive detector 1420, or a data collecting system 1430. The system according to the present disclosure may be implemented through circular orbit scanning, or also may be implemented through spiral trajectory scanning, and may be used for three-dimensional spectral CT imaging.

The photon-counting detector or energy-sensitive detector 1420 may include a plurality of pixels and is configured to receive and process photons passing through an object. The photon-counting detector or energy-sensitive detector 1420 may be, for example, an area-array detector or annular detector. According to some embodiments of the present disclosure, the photon-counting detector or energy-sensitive detector 1420 includes an electronics system 1425.

The ray generating device 1405 may include a ray source and is configured to emit, for example, X-ray.

The mechanical movement system 1410 is configured to cause a relative movement between an imaged object and the ray source. The mechanical movement system 1410 may include, for example, a mechanical movement device and a corresponding control system (not shown). The imaged object 1415 may move while the ray source and/or the detector 1420 keeps still (as shown in FIG. 1), or the ray source and/or the detector may move while the object keeps still. Generally, turning patients around is avoided in the medical field, which may be implemented by rotating a source and/or a detector. In the industrial non-destructive inspection, manners of rotating and translating objects are relatively common. For CT imaging, what works is relative movement, and thus the two manners are equivalent.

The data collecting system 1430 is configured to perform data collection on a photon passing through the imaged object 1415 from the photon-counting detector or energy-sensitive detector 1420.

The spectral CT imaging system 1400 may further include a master controller 1440 and an image reconstruction system 1435. The master controller 1440 is in charge of master control of the running process of the spectral CT system, including mechanical rotation, electrical control, safety interlock control, and so on. The image reconstruction system 1435 is configured to process data obtained by the data collecting system 1430 to obtain an attenuation coefficient image of the spectral CT in an energy window. The master controller 1440 and the image reconstruction system 1435 may be single PCs or may be workstations or computer clusters.

Figure 15:
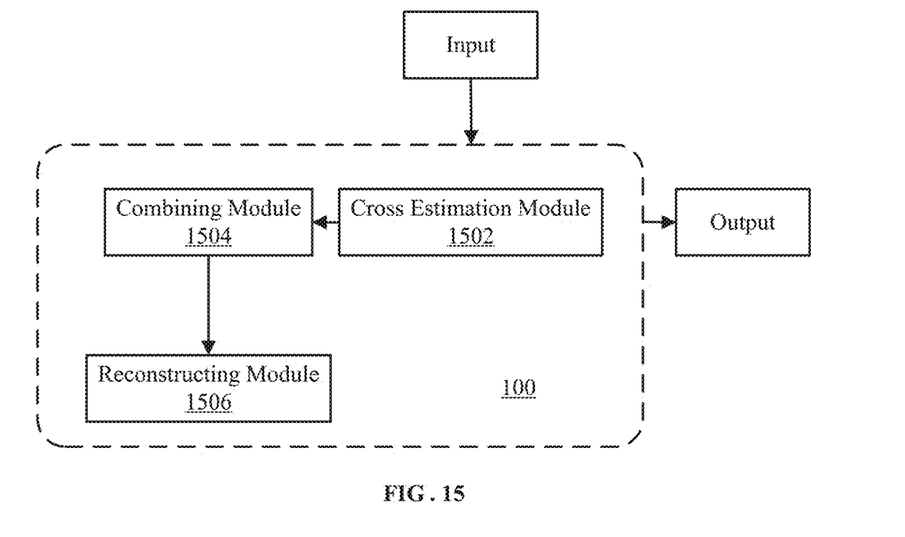
FIG. 15 schematically illustrates modules constituting an image reconstruction system according to some exemplary embodiments of the present disclosure.

FIG. 15 schematically illustrates modules of the image reconstruction system according to some exemplary embodiments of the present disclosure.

As shown in FIG. 15, the image reconstruction system includes a cross estimation module 1502, a combining module 1504, and a reconstructing module 1506.

The cross estimation module 1502 is configured to perform a projection data cross estimation using corresponding original projection data in at least one pair of energy windows constituted by different energy windows of the plurality of energy windows to obtain estimated projection data. Each pair of energy windows includes a first energy window and a second energy window.

The combining module 1504 is configured to combine the original projection data with the corresponding estimated projection data to obtain complete projection data.

The reconstructing module 1506 is configured to reconstruct the spectral CT image using the complete projection data.

According to some embodiments, the cross estimation module 1502 is configured to: establish, on an image domain, a mapping relation between image data in the first energy window and image data in the second energy window; obtain estimated image data using the mapping relation; and obtain the estimated projection data from the estimated image data.

The image reconstruction system as shown in FIG. 15 may be configured to achieve the foregoing reconstruction method according to the present disclosure, which is not described any more.

Through the above detailed description, those skilled in the art readily understand that the system and method according the embodiments of the present disclosure have one or more of the following advantages.

The reconstruction method and system according the embodiments of the present disclosure may be applied to the field of non-destructive inspection, medical diagnosis, safety inspection and the like. Compared with the existing reconstruction algorithm based on compressed sensing and a prior image (generally data at a single energy are used, or multi-energy data must be employed to perform determinant order minimization), the method according to the embodiment of the present disclosure may obtain more projection data by using, for example, an artificial neural network to learn a mapping relation among dual-energy absorption coefficients. The artificial neural network may adopt online learning, and the projection data passing through the identical ray path are extracted, during reconstruction, as the training data, and may be adapted to the mapping relation among various unknown and complex absorption coefficients at different energies. The method may be applicable to solving the problem of incomplete data reconstruction under the condition that the projection data at different energies have a subset of a part of the projection data passing through the identical ray path, for example, limited angle and sparse sampling and the like, and the method has a good effect.

The method according to the embodiment of the present disclosure may greatly reduce the data size required for reconstruction, is applicable to angle sparse sampling, sparse detector sampling and the like, may reduce the number of the detectors and the radiation dose to reduce the manufacturing cost of the CT system, may be used for reducing the angle coverage to reduce the z axis layer thickness and improve the time resolution, and thus has strong practicability and a wide scope of application.

The method according to the embodiment of the present disclosure may effectively inhibit artifacts possibly caused by reduction of data. In terms of reducing the data projection of the spectral CT, if two energies only cover an angle of 90 degrees respectively, the reconstruction effect obtained by using this method may be equivalent to the effect of independent reconstruction of each energy of the dual-energy CT covering an angle of 150 degrees respectively.

With description of the above embodiments, it will be readily understood by those skilled in the art that the embodiments of the present disclosure may be implemented by hardware or by means of software in combination with the necessary hardware. Thus, the technical solution according to the embodiments of the present disclosure may be embodied in the form of a software product which may be stored on a nonvolatile storage medium (which may be CD-ROM, flash memory, mobile hard disk and the like), including a number of instructions for enabling a computing device (which may be a personal computer, a server, a mobile terminal, or a network device and the like) to perform the method according to the embodiments of the present disclosure.

It will be understood by those skilled in the art that the drawings are merely schematic diagrams of exemplary embodiments and that the modules or processes in the drawings are not indispensably necessary to implement the present disclosure and are therefore not intended to limit the scope of protection of the present disclosure.

It will be understood by those skilled in the art that the above-described modules may be distributed in the apparatus as described in the embodiments, or may be modified in one or more devices different from the present embodiment. The modules of the above-described embodiments may be combined into one module or may be further divided into a plurality of submodules.

Exemplary embodiments of the present disclosure are particularly shown and described as above. It is to be understood that the present disclosure is not limited to the disclosed embodiments, but rather that the present disclosure is intended to cover various modifications and equivalent arrangements included within the spirit and scope of the appended claims.

The invention claimed is:

1. A spectral CT image reconstructing method, comprising:
    collecting incomplete original projection data in each of a plurality of energy windows;
    performing a projection data cross estimation using corresponding original projection data in at least one pair of energy windows constituted by different energy windows of the plurality of energy windows to obtain estimated projection data, wherein each pair of energy windows comprises a first energy window and a second energy window;

combining the original projection data with the corresponding estimated projection data to obtain complete projection data; and reconstructing a spectral CT image using the complete projection data, wherein the performing a projection data cross estimation using corresponding original projection data in at least one pair of energy windows constituted by different energy windows of the plurality of energy windows to obtain estimated projection data comprises:

establishing, on an image domain, a mapping relation between image data in the first energy window and image data in the second energy window;

obtaining estimated image data using the mapping relation; and obtaining the estimated projection data from the estimated image data, and wherein the establishing, on an image domain, a mapping relation between image data in the first energy window and image data in the second energy window comprises:

extracting, from the corresponding original projection data of the first energy window and of the second energy window, first identical projection data in the first energy window and second identical projection data in the second energy window passing through an identical ray path;

reconstructing using the first identical projection data to obtain first training image data;

reconstructing using the second identical projection data to obtain second training image data; and establishing, by means of a machine learning method using the first training image data and the second training image data, a first mapping relation from the image data in the first energy window to the image data in the second energy window and/or a second mapping relation from the image data in the second energy window to the image data in the first energy window.

2. The spectral CT image reconstructing method according to claim 1, wherein obtaining estimated image data using the mapping relation comprises:

respectively obtaining first initial image data and/or second initial image data by reconstructing in advance using the corresponding original projection data in the first energy window and the second energy window; and obtaining second estimated image data in the second energy window by mapping the first initial image data by means of the first mapping relation, and/or obtaining first estimated image data in the first energy window by mapping the second initial image data by means of the second mapping relation.

3. The spectral CT image reconstructing method according to claim 2, wherein the obtaining the estimated projection data from the estimated image data comprises:

obtaining first estimated projection data using the first estimated image data and a projection operator used in the first energy window, and/or obtaining second estimated projection data using the second estimated image data and a projection operator used in the second energy window.

4. The spectral CT image reconstructing method according to claim 1, wherein the collecting incomplete original projection data in each of a plurality of energy windows comprises limited angle sampling, angle sparse sampling, or sparse detector sampling.

5. A spectral CT imaging system, comprising:

a ray generating device, comprising a ray source;

a photon-counting detector or an energy-sensitive detector, comprising a plurality of pixels;

a data collecting system, configured to perform data collection on a photon passing through an imaged object from the photon-counting detector or energy-sensitive detector; and an image reconstruction system, configured to reconstruct a spectral CT image using data acquired by the data collecting system, wherein the data collecting system is configured to collect incomplete original projection data in each of a plurality of energy windows; and the image reconstruction system comprises a processor configured to:

perform a projection data cross estimation using corresponding original projection data in at least one pair of energy windows constituted by different energy windows of the plurality of energy windows to obtain estimated projection data, wherein each pair of energy windows comprises a first energy window and a second energy window;

combine the original projection data with the corresponding estimated projection data to obtain complete projection data; and reconstruct the spectral CT image using the complete projection data, wherein the processor is further configured to:

establish, on an image domain, a mapping relation between image data in the first energy window and image data in the second energy window;

obtain estimated image data using the mapping relation; and obtain the estimated projection data from the estimated image data, and wherein the processor configured to establish, on an image domain, a mapping relation between image data in the first energy window and image data in the second energy window is configured to:

extract, from the corresponding original projection data of the first energy window and of the second energy window, first identical projection data in the first energy window and second identical projection data in the second energy window passing through an identical ray path;

reconstruct using the first identical projection data to obtain first training image data;

reconstruct using the second identical projection data to obtain second training image data; and establish, by means of a machine learning method using the first training image data and the second training image data, a first mapping relation from the image data in the first energy window to the image data in the second energy window and/or a second mapping relation from the image data in the second energy window to the image data in the first energy window.

6. The spectral CT imaging system according to claim 5, wherein the processor configured to obtain estimated image data using the mapping relation is configured to:

respectively obtain first initial image data and/or second initial image data by reconstructing in advance using the corresponding original projection data in the first energy window and the second energy window; and obtain second estimated image data in the second energy window by mapping the first initial image data by means of the first mapping relation, and/or obtain first estimated image data in the first energy window by mapping the second initial image data by means of the second mapping relation.

7. The spectral CT imaging system according to claim 6, wherein the processor configured to obtain the estimated projection data from the estimated image data is configured to:

obtain first estimated projection data using the first estimated image data and a projection operator used in the first energy window, and/or obtain second estimated projection data using the second estimated image data and a projection operator used in the second energy window.

8. A non-transitory computer-readable storage medium having stored therein instructions that, when executed by a processor of a spectral CT imaging system, causes the system to perform a spectral CT image reconstructing method, the method comprising:

collecting incomplete original projection data in each of a plurality of energy windows;

performing a projection data cross estimation using corresponding original projection data in at least one pair of energy windows constituted by different energy windows of the plurality of energy windows to obtain estimated projection data, wherein each pair of energy windows comprises a first energy window and a second energy window;

combining the original projection data with the corresponding estimated projection data to obtain complete projection data; and reconstructing a spectral CT image using the complete projection data, wherein the performing a projection data cross estimation using corresponding original projection data in at least one pair of energy windows constituted by different energy windows of the plurality of energy windows to obtain estimated projection data comprises:

establishing, on an image domain, a mapping relation between image data in the first energy window and image data in the second energy window;

obtaining estimated image data using the mapping relation; and obtaining the estimated projection data from the estimated image data, and wherein the establishing, on an image domain, a mapping relation between image data in the first energy window and image data in the second energy window comprises:

extracting, from the corresponding original projection data of the first energy window and of the second energy window, first identical projection data in the first energy window and second identical projection data in the second energy window passing through an identical ray path;

reconstructing using the first identical projection data to obtain first training image data;

reconstructing using the second identical projection data to obtain second training image data; and establishing, by means of a machine learning method using the first training image data and the second training image data, a first mapping relation from the image data in the first energy window to the image data in the second energy window and/or a second mapping relation from the image data in the second energy window to the image data in the first energy window.

\* \* \* \* \*